United States Patent [19]

Love et al.

[11] 3,933,873

[45] Jan. 20, 1976

[54] PREPARATION OF OMEGA-AMINOALKANOIC ACIDS

[75] Inventors: Richard F. Love, Fishkill; Mahmoud S. Kablaoui, Wappinger Falls; Roger G. Duranleau, Ardonia, all of N.Y.

[73] Assignee: Texaco Inc., New York, N.Y.

[22] Filed: June 10, 1974

[21] Appl. No.: 477,712

Related U.S. Application Data

[63] Continuation-in-part of Ser. No. 206,197, Dec. 8, 1971, Pat. No. 3,816,404.

[52] U.S. Cl. ............................ 260/404; 260/534 R
[51] Int. Cl.² ........................................ C07C 99/00
[58] Field of Search ....................... 260/404, 534 R

[56] References Cited
UNITED STATES PATENTS

| | | | |
|---|---|---|---|
| 2,998,437 | 8/1961 | Benton | 260/404 |
| 3,557,166 | 1/1971 | Lachowicz et al. | 260/404 X |
| 3,816,404 | 6/1974 | Kablaoui et al. | 260/239.3 A |

*Primary Examiner*—Patrick P. Garvin
*Attorney, Agent, or Firm*—T. H. Whaley; C. G. Ries; George J. Darsa

[57] ABSTRACT

A method for preparing omega-aminoalkanoic acids by the steps of (1) nitro-oxidizing a cycloalkene to a cyclic alpha-nitroketone, (2) cleaving and esterifying a cyclic alpha-nitroketone with an alcohol to form an alkyl omega-nitroester, (3) catalytically hydrogenating the nitroester to an aminoester and (4) hydrolyzing the aminoester to an aminoalkanoic acid.

27 Claims, No Drawings

PREPARATION OF OMEGA-AMINOALKANOIC ACIDS

CROSS REFERENCE TO RELATED APPLICATION

This application is a continuation-in-part of our co-pending application Ser. No. 206,197, filed Dec. 8, 1971 now U.S. Pat. No. 3,816,404.

This invention relates to a novel method for preparing aminoalkanoic acids from cyclic olefins. In particular, this invention relates to a method for preparing omegaaminoalkanoic acids in the absence of the formation of large quantities of by-products.

BACKGROUND OF THE INVENTION

Heretofore, omega-aminoalkanoic acids were prepared by rearrangement of cycloalkanone oximes in oleum followed by hydrolysis and neutralization of the excess sulfuric acid with ammonia to produce between two and six pounds of ammonium sulfate per pound of acid. The various prior processes differed in the preparation of the cycloalkanone oximes. A serious disadvantage common to all of the earlier processes is the formation of large quantities of the byproduct ammonium sulfate which is not easily saleable.

Omega-aminoalkanoic acids are valuable materials employed in the production of fibers and resins, particularly Nylon-8 and Nylon-12. As such, a process capable of providing the acids which simultaneously does not produce ammonium sulfate as a by-product would be highly desirable.

It is therefore an object of this invention to provide a method for the preparation of omega-aminoalkanoic acids.

Another object of this invention is to provide a method for the preparation of omega-aminoalkanoic acids from cyclic olefins.

Yet another object of this invention is to provide a method for the preparation of omega-aminoalkanoic acids in high yields and in the absence of forming substantial amounts of by-products such as ammonium sulfate.

Other objects and advantages will become apparent from a reading of the following detailed description and examples.

SUMMARY OF THE INVENTION

Broadly, this invention contemplates a method for preparing omega-aminoalkanoic acids which comprises:

a. simultaneously contacting a solution containing a cycloalkene, a denitrating agent and an aprotic organic solvent with dinitrogen tetroxide and oxygen, where the mole ratio of cycloalkene to denitrating agent is about 0.5:1 to about 2:1, thereby forming 2-nitrocycloalkanone, b. contacting the 2-nitrocycloalkanone with an alcohol in a non-aqueous environment at a temperature of from about 20 to 200°C. thereby forming an alkyl omeganitroalkanoate, c. contacting said alkyl omega-nitroalkanoate with hydrogen and a Group VIII metal catalyst at a temperature of from 20° to 300°C. and under a hydrogen pressure of 500 to 1500 p.s.i.g. thereby forming an alkyl omega-aminoalkanoate, and d. contacting said alkyl omega-aminoalkanoate with water at a temperature of from 150° to 300°C.

STAGE ONE

According to this invention $C_7$ to $C_{20}$, preferably $C_7$ to $C_{12}$ cycloalkenes are converted to omega-aminoalkanoic acids by initially forming a solution composed of the cycloalkene, a denitrating agent and an organic solvent and contacting the solution with a mixture of dinitrogen tetroxide and oxygen at a temperature between about 0° to 40°C., preferably from 5° to 15°C. Temperatures in excess of 40°C. are undesirable because of the threat of explosion and temperatures below 0°C. require excessive refrigeration thereby rendering the process economically unattractive.

The ratio of the individual components in the first stage of the instant method represents an important aspect insofar as providing a process leading to high yields of the acid. Specifically, the mole ratio of cycloalkene to oxygen to dinitrogen tetroxide in the single step nitrooxidation reaction is maintained between about 1:1:0.5 and 1:30:1.5. It has been found that the presence of an aprotic organic solvent permits the mole ratio of denitrating agent to cycloalkene of above about 0.5:1 to about 2:1, preferably 0.8:1 to 1.3:1, during the nitrooxidation reaction to be maintained at levels heretofore considered inoperatively low. We have found that when conversion is conducted in the presence of the organic solvent, a significant economic benefit is realized in that lesser amounts of costly denitrating agent are needed, whereas in the absence of solvent amounts of denitrating agent several times that employed herein would be required to provide results comparable to that realized by the instant method. Ratios of denitrating agent below that specified above are undesirable because of the formation of by-products such as nitronitrates and nitroalcohols. The use of denitrating agent in amounts exceeding that specified results in excessive losses of agent, which losses may be reduced but not eliminated through the use of extensive separation and recovery procedures. The reaction time for this stage is generally between one half and five hours although longer and shorter periods may be employed depending upon the amount and rate of addition of dinitrogen tetroxide.

It will be appreciated that the nitrating agent, dinitrogen tetroxide, is an equilibrium mixture of dinitrogen tetroxide and nitrogen dioxide with equilibrium driven essentially to 100 percent dinitrogen tetroxide at 0°C. and essentially 100 percent nitrogen dioxide at 140°C. The term dinitrogen tetroxide as used herein denotes the equilibrium mixture as well as the pure $N_2O_4$ compound. Oxygen employed herein may be in pure form or diluted with air or in admixture with inert gases such as nitrogen or argon.

The cyclic alkenes contemplated herein correspond to the formula:

where R is a polymethylene radical of from 5 to 18 carbons, preferably 5 to 10, illustrated by cycloheptene, cyclooctene, cyclononene, cyclodecene, cycloundecene, cyclododecene, cyclotetradecene, cyclohexadecene, cyclooctadecene and cycloeicosene.

In the practice of this first stage, cycloalkene and denitrating agent are admixed with an aprotic organic solvent having a boiling point between about 30° to 100°C. Polar and protic solvents should be avoided in that their use results in the formation of mixtures composed of nitroketone, nitronitrate and nitroalcohol. The ratio of aprotic organic solvent to cycloalkene employed can range from 2:1 to 20:1 parts by weight. The product of the first stage reaction, namely 2-nitrocycloalkanone, can be recovered in admixture with the aprotic solvent if desired. Alternatively, by employing the specified solvent an additional benefit is imparted to the instant method in that the nitroketone may be recovered from the reaction mixture by means of distillation and extraction. Illustrative of the aprotic solvents which can be utilized in the first stage of this method we mention non-polar aprotic solvents such as n-hexane, n-heptane, carbon tetrachloride, cyclohexane, benzene and petroleum ether. In addition polar, aprotic solvents such as diethylether, tetrahydrofuran and dioxane can be employed. Preferably we utilize non-polar aprotic solvents. Thereafter, dinitrogen tetroxide is introduced to the solution containing cycloalkene, denitrating agent and solvent at a rate of between about 0.001 and 0.1 gram per minute per gram of cycloalkene, along with oxygen introduced at the rate of about 1:1.5 to 10:1.5 grams per gram of dinitrogen tetroxide.

Among the denitrating agents contemplated in the instant invention are those selected from group consisting of

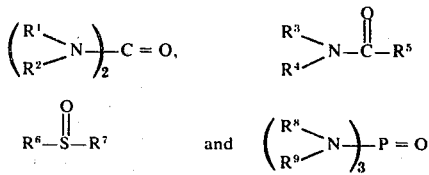

where $R^1$, $R^2$, $R^6$, $R^7$, $R^8$ and $R^9$ are alkyl from 1 to 5 carbons and $R^3$, $R^4$ and $R^5$ are hydrogen or alkyl from 1 to 5 carbons. Specific examples of the denitrating agent contemplated herein are dimethyl formamide, diethyl formamide, dimethyl acetamide, dimethyl sulfoxide, diethyl sulfoxide, tetramethylurea, tetraethylurea and hexamethylene phosphoramide. In addition, other denitrating agents such as 1-methyl-2-pyrrolidinone can be used. Particularly preferred denitrating agents are dimethyl formamide, diethyl sulfoxide and 1-methyl-2-pyrrolidinone.

Illustrative of the 2-nitrocycloalkanones formed in the first stage we mention 2-nitrocycloheptanone, 2-nitrocyclooctanone, 2-nitrocyclononanone, 2-nitrocyclodecanone, 2-nitrocycloundecanone and 2-nitrocyclododecanone.

STAGE TWO

In the second stage of the instant method, the 2-nitrocycloalkanone prepared above corresponding to the formula

where R is as heretofore defined is contacted with an alcohol wherein the cyclic nitroketone is cleaved and esterified at temperatures of from 20° to 200°C. to an alkyl omeganitroalkanoate. In practice, mole ratios of 2-nitrocycloalkanone to alcohol of from 1:1 to 1:100, preferably 1:5 to 1:25, are employed.

Alcohols employed in this stage of the method correspond to the formula R'OH and include primary and secondary alcohols. Tertiary alcohols have not been found to be reactive. Thus, in the formula above R' can be an alkyl group of from 1 to 20 carbon atoms such as methyl, ethyl, propyl, butyl, hexyl, octyl, decyl, dodecyl or hexadecyl. Dihydroxy and polyhydroxy primary and secondary alcohols are also intended to be understood as operative in the instant process. Illustrative of the alcohols contemplated herein we mentioned methanol, ethanol, isopropanol, n-butanol, 2-hexanol, cyclohexanol, 2-octanol, 2-decanol, 1-dodecanol, 1-hexadecanol, ethylene glycol, propylene glycol and pentaerythritol. Mixtures of alcohols such as $C_{10}$ to $C_{13}$ alcohols are contemplated including isomeric mixtures containing primary and secondary alcohols.

In one embodiment, cleavage and esterification can be undertaken thermally, that is, in the absence of a catalytic agent, employing temperatures of from about 50° to 200°C., preferably from 100° to 190°C. In another embodiment, cleavage and esterification can be accomplished catalytically employing a basic catalyst at temperatures of from 20° to 120°C., preferably 60° to 100°C. In practice catalytic reactions below 20°C. are excessively slow. Conversely, thermal reactions exceeding 200°C. are deleterious in that thermal decomposition of the cyclic nitroketone to a mixture of products occurs rather than the desired cleavage and esterification. Pressures of from 0 to 500 p.s.i.g. may be employed. Specifically, thermal conversions are preferably conducted at pressures of 0 to 500 p.s.i.g. and the catalytic conversion conducted at pressures of 0 to 40 p.s.i.g.

Most importantly, this stage of the process must be conducted in a non-aqueous environment, that is, in the substantial absence of water. The cleavage and esterification reaction, whether conducted thermally or catalytically is sensitive to water and water in amounts exceeding 0.1 weight percent based on the weight of alcohol employed cause competing reactions to occur leading to the formation of acids in this stage instead of the desired ester. Formation of acids is undesirable inasmuch as they cause the hydrogenation catalyst employed in the subsequent stage to lose activity. In a highly preferred aspect of this invention, absolute alcohols are used. Excessive amounts of alcohol can be employed serving as solvent for the reaction or alternatively in inert reaction solvent may be utilized such as n-hexene, n-heptane, xylene, ethylbenzene, dichlorobenzene, methylnaphthalene, dioxane and tertiary alcohols. The reaction times for the second stage range from a few minutes to two hours.

With regard to the second stage embodiment involving catalytic cleavage and esterification, the basic catalysts contemplated herein are oxides, hydroxide and salts of the metals of Groups IA and IIA of the Periodic Table exemplified by sodium hydroxide, sodium carbonate, sodium fluoride, sodium acetate, sodium decanoate, potassium hydroxide, potassium carbonate, potassium fluoride, potassium acetate, potassium octanoate, calcium oxide, calcium carbonate, calcium fluoride, calcium propionate, barium oxide, barium carbonate, barium fluoride and barium hexanoate. Other basic catalysts include tertiary amines such as trimethylamine and triethylamine. Highly preferred catalysts are sodium carbonate, postassium carbonate and potassium fluoride. In accordance with this second stage embodiment, 2-nitrocycloalkanone and the alcohol are contacted with the catalyst in a weight ratio of catalyst to nitroketone between about 0.01:1 and 0.2:1, thereby forming an alkyl omega-nitroalkanoate corresponding to the formula:

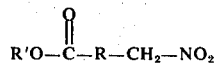

when R and R' are as heretofore defined. At the completion of this reaction, catalyst, when employed, is separated as for example by filtration and excess alcohol and solvent, if present, are removed by distillation. The alkyl omega-nitroalkanoate product such as methyl 7-nitroheptanoate, ethyl 7-nitroheptanonate, methyl 8-nitrooctanoate, propyl 8-nitrooctanoate, methyl 9-nitrononoate, cetyl 9-nitrononoate, methyl 10-nitrodecanoate, ethyl 10-nitrodecanoate, methyl 11-nitroundecanoate, methyl 12-nitrododecanoate, ethyl 12-nitrododecanoate, butyl 12-nitrododecanoate, methyl 14-nitrotetradecanoate, methyl 16-nitrohexadecanoate and methyl 20-nitroeicosanoate is substantially free of byproducts.

STAGE THREE

In the third stage of the method, the alkyl omega-nitroalkanoate is hydrogenated to an alkyl omega-aminoalkanoate by contacting with hydrogen and a Group VIII metal catalyst for a period of ½ to 5 hours at a temperature of from 20° to 300°C., preferably 100° to 220°C., under hydrogen pressures of from 500 to 1500 p.s.i.g. Illustrative of the Group VIII metal catalysts we mention the oxides, hydroxides and salts of the metals platinum, palladium, rhodium, ruthenium, iron, cobalt, nickel, iridium and osmium including mixtures thereof as for example platinum oxide, palladium chloride, Raney nickel, nickel on kieselguhr, platinum on carbon, ruthenium on carbon, rhodium on carbon, iron oxide and cobalt on silica. The metals may themselves also be employed including platinum, palladium, rhodium, ruthenium and nickel.

The preferred and convenient solvents for the hydrogenation are the alcohols used in Stage Two. This permits the reduction to occur in the solution from stage two without necessitating the separation of alcohol and, if employed, solvent thereby improving the efficiency of the process. Other solvents can be used in Stage Three and among those contemplated are pentane, heptane, decalin, tetrahydrofuran, triethylamine and dimethylaniline. At the completion of the third stage, the product obtained comprises from 88 to 98 percent of the alkyl omega-aminoalkanoate. A particular advantage of stages two and three of the instant method resides in the ability to essentially convert all of the 2-nitrocycloalkanone to alkyl omega-aminoalkanoate.

STAGE FOUR

In the fourth stage of the method, the alkyl omega-aminoalkanoate of the formula:

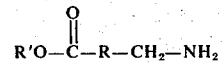

where R and R' are as heretofore defined, is contacted with water at a temperature of from about 150° to 300°C. at autogenous pressure, suitably 50 to 1200 p.s.i.g. thereby forming aminoalkanoic acid of the formula:

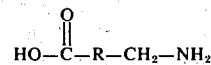

The hydrolysis of the aminoester is undertaken employing from about 1 to 200, preferably 20 to 100, moles of water per mole of aminoester in a non-oxidizing environment. A plurality of non-oxidizing environments can be used including such gases as nitrogen, methane, argon, helium, neon, ethane, propane, hydrogen and mixtures thereof such as hydrogen and light hydrocarbons. As a co-product, the alcohol R'OH can be recovered from the acid by distillation.

The omega-aminoalkanoic acids prepared by this process are useful as surfactants and lubricant additives. Further, they are useful as intermediates in the preparation of polyamides such as Nylon-8 and Nylon-12.

In order to more fully illustrate the nature of this invention and the manner of practicing the same the following examples are presented.

EXAMPLE I

STAGE ONE

Into a 500 milliliter 3 neck flask equipped with a thermometer, condenser and gas inlet, there was charged 33.2 grams (0.20 mole) of cyclododecene, 20 milliliters (0.258 mole) of dimethyl formamide and 200 milliliters of benzene. To this solution maintained at temperature of 10°C. there was introduced a mixture of dinitrogen tetroxide and oxygen, 18.5 grams (0.201 mole) of dinitrogen tetroxide and 32 grams (1 mole) of oxygen over a period of four hours. Oxygen addition was continued for 30 minutes. The benzene solution was diluted with 100 ml. of ether and washed with three 150 milliliter portions of water to remove dimethyl formamide and nitric acid. The organic phase was separated and the solvent stripped under reduced pressure (25–30 mm. Hg.) to yield 45.7 grams of a residue identified by infrared and nuclear magnetic resonance analyses to be 91 percent 2-nitrocyclododecanone.

STAGE TWO

To 22.4 grams (100 moles) of 2-nitrocyclododecanone there was added 300 milliliters (7.5 moles) of methanol in a presssure reactor. 3.0 grams of nickel on silica catalyst was added at this point for convenience and does not take part in the reaction. The solution was heated to a temperature of 149°C. for 45 minutes thereby forming methyl 12-nitrododecanoate.

STAGE THREE

Thereafter, the reactor was pressurized to 1000 p.s.i.g. with hydrogen and reaction was kept at 149°C. for 4 hours. The reaction mixture was filtered to remove the catalyst, methanol stripped therefrom by distillation and a residue weighing 21.9 grams (95 percent yield) was obtained and identified by infrared and nuclear magnetic resonance analyses to be methyl 12-aminododecanoate.

STAGE FOUR

Methyl 12-aminododecanoate (21.8 grams) and 300 ml. (16.6 moles) of water were heated in a stirred autoclave at 300°F., for 2 hours under nitrogen. Thereafter, the reactor was cooled, the contents removed and water evaporated under reduced pressure. The gray crystalline residue (19.6 grams, 95 percent yield) was identified as 12-aminododecanoic acid.

EXAMPLE II
STAGE ONE

A rapidly stirred solution of cyclooctene (11.0 grams, 100 mmoles) and dimethylformamide (15 ml., 200 mmoles) in 200 ml. (2.1 moles) of dry benzene, cooled to 5°C. was treated with a mixture of dinitrogen tetroxide (9.2 grams, 100 mmoles) and oxygen (12.8 grams, 400 mmoles) over a period of three hours. The admission of oxygen was continued over a period of 30 minutes and the mixture warmed to ambient temperature. The benzene solution was diluted with an equal volume of ether, extracted with three 100 ml. portions of water to remove nitric acid and dimethylformamide. The organic phase was separated and the solvent stripped under reduced pressure (25–30 mm. Hg.). The residue, 16.8 grams, consisted of 93 percent 2-nitrocyclooctanone as identified by nuclear magnetic resonance.

STAGE TWO

To 200 ml. (4.95 moles) of dry methanol, there was added 15.8 grams (92.5 mmoles) of 2-nitrocyclooctanone and 0.3 gram of platinum oxide catalyst. The reactor was flushed with nitrogen, heated to 149°C. for 45 minutes. The catalyst was added at this point for convenience and does not take part in the reaction. Methyl 8-nitrooctanoate was formed.

STAGE THREE

Thereafter, the reactor was cooled to 38°C., pressurized with hydrogen to 1000 p.s.i.g. and heated to 149°C. for 4 hours. After cooling, the reactor contents were filtered free of catalyst and stripped of solvent. The residue, 14 grams (88 percent yield) was identified as methyl 8-aminooctanoate by infrared and nuclear magnetic resonance.

STAGE FOUR

A mixture of 13 grams of methyl 8-aminooctanoate (68 mmoles) and 200 ml. of water (11.1 moles) were heated for 2 hours at 177°C. under nitrogen. Upon cooling, the contents were removed and water stripped under reduced pressure. The residue (10.3 grams, 95 percent yield) was identified by infrared and nuclear magnetic resonance to contain 8-aminooctanoic acid.

We claim:
1. A method for preparing omega-aminoalkanoic acids which comprises:
   a. simultaneously contacting at a temperature between about 0° to 40°C. a solution containing a $C_7$ to $C_{20}$ cycloalkene, a denitrating agent and an aprotic organic solvent with dinitrogen tetroxide and oxygen, wherein said denitrating agent is selected from the group consisting of 2-pyrrolidinones,

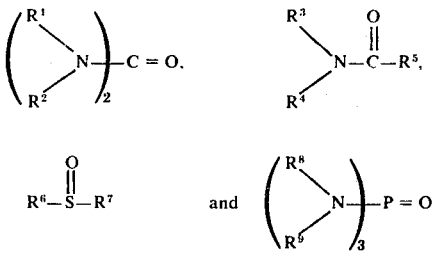

where $R^1$, $R^2$, $R^6$, $R^7$, $R^8$ and $R^9$ are alkyl of from 1 to 5 carbons and $R^3$, $R^4$ and $R^5$ are hydrogen or alkyl of from 1 to 5 carbons, where the mole ratio of cycloalkene to denitrating agent is above about 0.5:1 to about 2:1, thereby forming 2-nitrocycloalkanone,
   b. contacting 2-nitrocycloalkanone with an alcohol, wherein said alcohol is a primary or secondary alcohol corresponding to the formula R'OH where R' is an alkyl group of from 1 to 20 carbon atoms, in a non-aqueous environment at a temperature of from about 20° to 200°C. thereby forming an alkyl omega-nitroalkanoate,
   c. contacting said alkyl omega-nitroalkanoate with hydrogen and a Group VIII metal catalyst at a temperature of from 20° to 300°C. under a hydrogen pressure of 500 to 1500 p.s.i.g. thereby forming an alkyl omega-aminoalkanoate, and
   d. contacting said alkyl omega-aminoalkanoate with water at a temperature of from 150° to 300°C.

2. A method according to claim 1 wherein said cycloalkene has from 7 to 12 carbon atoms.

3. A method according to claim 1 wherein said cycloalkene is cyclooctene.

4. A method according to claim 1 wherein said cycloalkene is cyclododecene.

5. A method according to claim 1 wherein said denitrating agent is dimethyl formamide.

6. A method according to claim 1 wherein said organic solvent has a boiling point of between about 30° to 100°C.

7. A method according to claim 1 wherein said contacting in (a) is conducted at a temperature between about 5° to 15°C.

8. A method according to claim 1 wherein the mole ratio of said denitrating agent to cycloalkene is about 0.8:1 to 1.3:1.

9. A method according to claim 1 wherein said organic solvent is carbon tetrachloride.

10. A method according to claim 1 wherein said organic solvent is benzene.

11. A method according to claim 1 wherein said alcohol in (b) is methanol.

12. A method according to claim 1 wherein step (b) is conducted thermally at a temperature of from 100° to 190°C.

13. A method according to claim 1 wherein step (b) is conducted in the presence of a basic catalyst at a temperature of from 60° to 100°C.

14. A method according to claim 13 wherein said catalyst is potassium fluoride.

15. A method according to claim 13 wherein said catalyst is sodium carbonate.

16. A method according to claim 1 wherein the mole ratio of 2-nitrocycloalkanone to alcohol in step (b) ranges from 1:1 to about 1:100.

17. A method according to claim 1 wherein said alkyl omega-nitroalkanoate in (b) is methyl 8-nitrooctanoate.

18. A method according to claim 1 wherein said alkyl omega-nitroalkanoate in (b) is methyl 12-nitrododecanoate.

19. A method according to claim 1 wherein said Group VIII metal catalyst is platinum oxide.

20. A method according to claim 1 wherein said Group VIII metal catalyst is nickel on kieselguhr.

21. A method according to claim 1 wherein said contacting in (c) is conducted at a temperature of 100° to 220°C.

22. A method according to claim 1 wherein said aminoester in (c) is methyl 8-aminooctanoate.

23. A method according to claim 1 wherein said aminoester in (c) is methyl 12-aminododecanoate.

24. A method according to claim 1 wherein from 1 to 200 moles of water per mole of said aminoester is employed in (d).

25. A method according to claim 1 wherein said contacting in (d) is at a pressure of 50 to 1200 p.s.i.g.

26. A method according to claim 1 wherein said acid is 12-aminododecanoic acid.

27. A method according to claim 1 wherein said acid is 8-aminooctanoic acid.

* * * * *